United States Patent [19]

Prasad et al.

[11] Patent Number: 5,898,074
[45] Date of Patent: *Apr. 27, 1999

[54] PROCESS FOR PREPARING 2-(METHYLTHIO)-5-(TRIFLUOROMETHYL)-1,3,4-THIADIAZOLE USING METHYLDITHIOCARBAZINATE AND A MOLAR EXCESS OF TRIFLUOROACETIC ACID WITH RECOVERY OF TRIFLUOROACETIC ACID

[75] Inventors: Vidyanatha A. Prasad, Leawood, Kans.; Achim Noack, Leichlingen, Germany

[73] Assignees: Bayer Corporation, Pittsburgh, Pa.; Bayer Aktiengesellschaft, Leverkusen, Germany

[ * ] Notice: This patent is subject to a terminal disclaimer.

[21] Appl. No.: 08/989,485

[22] Filed: Dec. 12, 1997

[51] Int. Cl.⁶ .................................................. C07D 285/12
[52] U.S. Cl. ............................................................ 548/136
[58] Field of Search ............................................... 348/136

[56] References Cited

U.S. PATENT DOCUMENTS

| | | | |
|---|---|---|---|
| 3,562,284 | 2/1971 | Newman et al. | 260/302 |
| 5,101,034 | 3/1992 | Schmidt et al. | 548/136 |
| 5,147,443 | 9/1992 | Diehr et al. | 71/67 |
| 5,162,539 | 11/1992 | Diehr | 548/136 |

OTHER PUBLICATIONS

Gyoefi and Csavassy, Acta Chimica Academiae Scientiarum Hungaricae, Tomus 82 (1): 91–97, (month unavailable) 1974.
Aldrich Catalog #30,203–1 p. 1461, 1996.

*Primary Examiner*—Robert Gerstl
*Attorney, Agent, or Firm*—Joseph C. Gil; Carol Marmo

[57] ABSTRACT

The present invention provides a process for preparing 2-(methylthio)-5-(trifluoromethyl)-1,3,4-thiadiazole. The process includes the steps of reacting methyldithiocarbazinate with a molar excess of trifluoroacetic acid and recovering the excess trifluoroacetic acid.

30 Claims, No Drawings

5,898,074

PROCESS FOR PREPARING 2-(METHYLTHIO)-5-(TRIFLUOROMETHYL)-1,3,4-THIADIAZOLE USING METHYLDITHIOCARBAZINATE AND A MOLAR EXCESS OF TRIFLUOROACETIC ACID WITH RECOVERY OF TRIFLUOROACETIC ACID

TECHNICAL FIELD OF THE INVENTION

The field of this invention is the synthesis of thiadiazoles. More particularly, this invention pertains to improved processes for making 2-(methylthio)-5-(trifluoromethyl)-1,3,4-thiadiazole using trifluoroacetic acid and methyldithiocarbazinate.

BACKGROUND OF THE INVENTION

Existing methods for preparing 2-(methylthio)-5-(trifluoromethyl)-1,3,4-thiadiazole are limited by the excessive cost of commercial scale application of laboratory procedures. Many existing reports provide little information on how reaction conditions and particular reactants would affect product yield or purity. In addition, use of procedures and reactions developed in the laboratory cannot always be directly applied to commercial scale production because such laboratory procedures typically involve the use of expensive reactants and or expensive (e.g., separation and purification procedures) techniques. U.S. Pat. No. 3,562,284 discloses a process for making certain 2-(alkylthio)-5-(halogenoalkyl)-1,3,4-thiadiazoles such as 2-(methylthio)-5-(trifluoromethyl)-1,3,4-thiadiazoles wherein methyldithiocarbazinate is reacted with a carboxylic anhydride (e.g., trifluoroacetic anhydride) or with a carboxylic acid (e.g., trifluoroacetic acid) in a solvent (e.g., toluene). The reaction can occur in the presence of phosphorous trichloride and pyridine with added sulfuric acid (DE-A-3,422,861) or with carbonyl chlorides (e.g., trifluoroacetyl chloride) and diethylene glycol dimethyl ether, as well as with pyridine and sulfuric acid (DE-A-3,722,320). The first-mentioned method is poorly suited for commercial, large-scale production because the reactants (anhydrides) are expensive and they are used in excess. The reaction with carboxylic acids, phosphorus trichloride, pyridine, sulfuric acid and carbonyl chlorides requires an extensive work-up procedure in which the pyridine is separated off and recovered. Further, phosphorus trichloride forms only sparingly soluble reaction products, which makes mixing difficult and produces unacceptable amounts of waste. Finally, the yields realized from such processes are unacceptably low.

Other procedures for making a 2-(substituted)-5-(trifluoromethyl)-1,3,4-thiadiazole involve the reaction of a carboxylic acid (e.g., trifluoroacetic acid) and a dithiocarbazic ester in the presence of a phosphorylchloride or polyphosphoric acid. (See, e.g., U.S. Pat. No. 5,162,539 and Gyoefi and Csavassy, *Acta Chimica Academiae Scientiarum Hungaricae, Tomus* 82 (1), (91–97, 1974). The use of such phosphorus compounds results in the formation of waste products containing unacceptably high levels of phosphates and, thus, creates an environmental hazard. Still further, this method requires the use of dry methyldithiocarbazinates (a toxic convulsant), the use of which in the dry state creates a severe industrial hygiene problem.

There is a need in the art, therefore, for an efficient, high yield, practical, safe method for the commercial, large-scale production of 2-(methylthio)-5 (trifluoromethyl)-1,3,4-thiadiazole. The present invention provides such a process.

BRIEF SUMMARY OF THE INVENTION

The present invention provides a process for preparing 2-(methylthio)-5-(trifluoromethyl)-1,3,4-thiadiazole. The process includes the steps of reacting methyldithiocarbazinate in a solvent with an excess of trifluoroacetic acid, removing water and excess TFA and recovering the TFA.

Trifluoroacetic acid is preferably present at a 10 to 500 percent molar excess relative to methyldithiocarbazinate. That is, the molar ratio of trifluoroacetic acid to methyldithiocarbazinate is from about 1.1:1 to about 5:1. More preferably, the molar ratio of trifluoroacetic acid to methyldithiocarbazinate is from about 1.25:1 to about 3.5:1 and, even more preferably from about 1.25:1 to about 2:1.

The reaction of trifluoroacetic acid and methyldithiocarbazinate occurs in the presence of a solvent. In one embodiment, the trifluoroacetic acid serves as the solvent. Preferably, however, the solvent is an aromatic co-solvent such as toluene, xylene, cumene or mesitylene. Toluene is especially preferred. With co-solvents, it is possible to reduce the TFA quantity compared to a reaction without co-solvents. The co-solvent is present in an amount of at least about 0.5 moles of co-solvent per mole of methyldithiocarbazinate. Preferably, the co-solvent is present in an amount of from about 1.5 moles to about 3.0 moles of co-solvent per mole of methyldithiocarbazinate and, more preferably in an amount of from about 2.5 moles to about 3.0 moles of co-solvent per mole of methyldithiocarbazinate.

The excess trifluoroacetic acid is recovered by either of two preferred means. In one embodiment, the excess trifluoroacetic acid is converted to a trifluoroacetic-alkali metal salt and free trifluoroacetic acid is released from the salt by acidifying the salt. Excess trifluoroacetic acid is converted to an alkali metal salt by reacting the excess acid with an alkali metal salt such as an alkali metal hydroxide. Preferred alkali metals are sodium, potassium and lithium. Sodium hydroxide is most preferred. The amount of alkali metal used relative to the amount of excess trifluoroacetic acid ranges from about 1 to about 2 moles of alkali metal per mole of excess trifluoroacetic acid. A molar ratio of 1.5:1 is preferred.

The formed salt is acidified with an inorganic acid such as hydrochloric acid, sulfuric acid or nitric acid. Hydrochloric acid is preferred. The hydrochloric acid can be added as a gas. In a preferred embodiment, water is mixed with the trifluoroacetic-alkali metal salt prior to acidification.

In a second and preferred embodiment, excess TFA is recovered by distillation. In accordance with this embodiment, the mixture of solvent (e.g., toluene), TFA and water is heated while azeotroping the solvent, TFA and water. Vapors from this azeotropic distillation are condensed, the toluene phase containing traces of TFA is recycled into the next batch and the TFA/water phase collected. The TFA/water phase is again distilled to purge water allowing for recovery and recycle of the TFA.

The recovered trifluoroacetic acid from either method can be recycled into the next batch where it reacts with methyldithiocarbazinate to form additional 2-(methylthio)-5-(trifluoromethyl)-1,3,4-thiadiazole.

DETAILED DESCRIPTION OF THE INVENTION

I. The Invention

The present invention provides novel processes for preparing 2-(methylthio)-5-(trifluoromethyl)-1,3,4-thiadiazole (TDA), an intermediate useful in the preparation of herbicides. The novel processes of this invention use methyldithiocarbazinate (MDTC) and trifluoroacetic acid (TFA) as the primary reactants. The processes allow for production of TDA in high yields with efficient means for removing by-products and recycling key reagents.

II. Process Using Excess Trifluoroacetic Acid

In one aspect, a process of the present invention for preparing 2-(methylthio)-5-(trifluoromethyl)-1,3,4-thiadiazole includes the steps of reacting methyldithiocarbazinate with an excess of trifluoroacetic acid, optionally in the presence of a co-solvent and removing water and excess trifluoroacetic acid.

MDTC prepared by any means can be used in a present process. Especially preferred means for preparing MDTC are disclosed in U.S. patent application Ser. Nos. 08/743,763, 08/743,764 and 0/743,775, all filed on Nov. 7, 1996. The disclosures of all those patent applications are incorporated herein by reference.

TFA is preferably present at a 10 to 500 percent molar excess relative to MDTC. That is, the molar ratio of TFA to MDTC (TFA:MDTC) is from about 1.1:1 to about 5:1. More preferably, the TFA:MDTC molar ratio is from about 1.25:1 to about 3.5:1 and, even more preferably from about 1.25:1 to about 2:1. As shown hereinafter in the Examples, increasing the molar excess of TFA relative to MDTC increases the yield of TDA (See Table 1).

The reaction preferably occurs at a temperature of from about 30° C. to about 150° C. and, more preferably from about 60° C. to about 140° C. Reaction times depend upon the temperature. Where the temperature is from about 80° C. to about 130° C., reaction time is from about 1 to about 5 hours.

The MDTC used in the present process can contain water. The ability to use "wet" MDTC offers a substantial benefit over existing processes that use only dry MDTC. MDTC is a known toxic substance and its use in dry form is likely to result in contamination of the air in processing plants with MDTC dust. This environmental hazard is substantially reduced if wet MDTC can be used. For use in the present process, MDTC can contain up to about 50 weight percent water.

Unlike prior art processes, water may be introduced into the reaction via recycle streams. The total amount of water in the reaction mixture is preferably less than about 30 grams of water per 0.5 moles of MDTC. As shown hereinafter in the Examples, the presence of 30 or less grams of water per 0.5 moles of MDTC has no deleterious effect on product formation. Increasing the amount of water to 40 grams or more resulted in reductions in product (TDA) yield.

The reaction of TFA and MDTC occurs in the presence of a solvent. In one embodiment, the trifluoroacetic acid itself serves as the solvent. Preferably, however, the solvent is an aprotic, aromatic co-solvent. Such co-solvents are well known in the art. Exemplary and preferred such co-solvents are toluene, xylene, cumene and mesitylene. Toluene is especially preferred.

The amount of solvent used can vary over a wide range as readily determined by a skilled artisan. The precise amount of solvent will depend on the particular solvent used. Where a co-solvent is used, it is present in an amount of at least about 0.5 moles of co-solvent per mole of MDTC. Preferably, the co-solvent is present in an amount of from about 1.5 moles to about 3.0 moles per mole of MDTC and, more preferably in an amount of from about 2.5 to about 3.0 moles of co-solvent per mole of MDTC. The reaction can proceed by mixing the entire desired amounts of MDTC and TFA. All other modes of addition are suitable as well.

The reaction mixture of MDTC and TFA can optionally include a catalyst. Exemplary such catalysts are p-toluenesulfonic acid, sulfuric acid, phosphoric acid, and polyphosphoric acids. Where a catalyst is used, it is present in an amount of about 2.0 grams per mole of MDTC. Water is formed as a reaction product of the MDTC and TFA reaction. Additional water may also be present because of recycle streams. Water is removed from the reaction mixture by an azeotropic distillation. The azeotropic removal of water is readily accomplished in the presence of the solvent, particularly where toluene is used as a co-solvent. The temperature required for the completion of the reaction is adequate for the azeotropic removal of the water and excess trifluoroacetic acid. Therefore, no additional work-up is required.

III. Recovery of Excess Trifluoroacetic Acid Using Base

In another aspect, the present invention provides a process for preparing TDA. The process includes the steps of reacting MDTC with a molar excess of TFA and recovering the excess TFA. As disclosed above in Section II, TFA is preferably present at a 10 to 500 percent molar excess relative to MDTC. Preferred molar ratios of TFA to MDTC are the same as set forth above.

The reaction conditions (e.g., temperature) and use of solvents are the same as set forth above. Where toluene is the co-solvent, it is present in an amount of from about 0.5 moles of toluene per mole of MDTC to about 3.5 moles of toluene per mole of MDTC. Preferably, toluene is present in an amount of from about 1.5 to about 3.0 moles of toluene per mole of MDTC and, more preferably in an amount of from about 2.5 to about 3.0 moles of toluene per mole of MDTC.

The excess TFA is recovered by first converting that TFA to a trifluoroacetic-alkali metal salt and then releasing free trifluoroacetic acid from the salt by acidifying the salt. Conversion of TFA to the salt is accomplished by reacting the excess acid with an alkali metal salt. Alkali metal salts suitable for converting acids to salts are well known in the art. Exemplary and preferred such alkali metal salts are alkali metal hydroxides such as NaOH, KOH and LiOH. Preferred alkali metals are sodium, potassium and lithium. Sodium hydroxide is most preferred. The amount of alkali metal relative to the amount of excess TFA ranges from about 1 to about 2 moles of alkali metal per mole of excess TFA. A molar ratio of 1.5:1 is preferred.

The formed trifluoroacetic-salt is then acidified to form free TFA. Formation of free TFA is accomplished by reacting the salt with a concentrated inorganic acid. Exemplary such acids are hydrochloric acid, sulfuric acid and nitric acid. Hydrochloric acid is preferred. The hydrochloric acid can be added as a gas. In a preferred embodiment, water is mixed with the trifluoroacetic-alkali metal salt prior to acidification. The recovered trifluoroacetic acid can be recycled into the original reaction mixture where it reacts with MDTC to form additional TDA.

IV. Recovery of TFA Using Distillation

In a preferred embodiment, excess TFA is recovered using distillation. In accordance with this embodiment, the reaction mixture containing MDTC, TFA, solvent and water is heated to a temperature sufficient for azeotropic separation of solvent and water. Where the solvent is toluene, heating is typically accomplished at a temperature of about 100° C. As a result of heating vapors are formed. The vapors are collected and allowed to condense by reducing the temperature. Condensation of the vapors results in the formation of an organic phase (e.g., toluene) and an aqueous phase, both of which phases contain TFA.

The TFA/solvent phase is directly recycled to the reaction mixture. The TFA/aqueous phase is distilled a second time to purge water from the TFA. The recovered TFA can then be recycled to the reaction mixture. A detailed description of the use of distillation to recover excess TFA is set forth hereinafter in the Examples.

The following Examples illustrate preferred embodiments of the present invention and are not limiting of the specification or claims in any way.

EXAMPLES

EXAMPLE 1

Production of 2-(methylthio)-5-(trifluoromethyl)-1,3,4-thiadiazole (TDA) Using MDTC and Excess TFA A. General Protocol—125 Grams (g) of toluene were charged to a flask. 67.9 Grams (0.5 moles) of methyldithiocarbazinate (MDTC)(90% A.I. with 5% water and 5% impurities) were added to the flask to form a slurry. 114 Grams of trifluoroacetic acid (TFA)(1.0 mole) were added to the slurry with agitation over 10 to 15 minutes without cooling. The temperature of the mixture rose to about 38° C. upon TFA addition. The mixture was heated to about 70° C. and maintained at that temperature for about 3 hours. The mixture was then heated to reflux (about 115° C.–116° C.) to remove water and any distillable TFA. This temperature was maintained for about 10 minutes until no aqueous phase separated from the condensate. The yield of TDA was about 90% to 93%.

B. Effects of Excess TFA—The reaction of MDTC and TFA was carried out as set forth above in (A) except that the amount of TFA relative to MDTC was varied. TDA yields were determined at each TFA level. The results are summarized below in Table 1.

TABLE 1

Effect of TFA Excess on TDA Yield
(2.7 moles toluene/mole MDTC)

| TFA Excess, % | Net Yield, % | % Bis-Isomer (Solvent Free) |
|---|---|---|
| 0 | 70.4 | 9.8 |
| 10 | 81.5 | 9.4 |
| 20 | 88.2 | 6.2 |
| 30 | 90.2 | 5.5 |
| 40 | 91.0 | 4.3 |
| 50 | 91.1 | 3.8 |
| 100 | 92.2 | 1.9 |
| 200 | 92.8 | 1.2 |

It can be seen from the data in Table 1 that increasing the molar excess of TFA increased the yield of TDA. The greatest increases in TDA yield were seen when the molar excess of TFA increased from 10% to about 100%. Increases in the molar excess of TFA from about 100% to about 200% resulted in only small gains in TDA yield.

C. Effects of Toluene as a Solvent—TDA was prepared in accordance with paragraph (A) above except that the level of toluene relative to the level of MDTC was varied. For these studies, 2 moles of TFA were reacted with one mole of MDTC. Summary data are shown in Table 2, below.

TABLE 2

Effect of Toluene on TDA Yield
(2.0 moles TFA/mole MDTC)

| Moles Toluene/Moles MDTC | % TDA net yield based on MDTC |
|---|---|
| 2.70 | 92.2 |
| 2.05 | 89.6 |
| 1.35 | 87.8 |
| 0.67 | 86.2 |

The data in Table 2 show that TDA yield increases with increasing levels of toluene. TDA yield did not improve substantially when toluene levels exceeded about 2.7 moles per mole of MDTC.

D. Effects of Water Levels—Water can be expected in the primary reaction from two main sources. First, the MDTC used in the reaction can contain up to about 50 weight percent water. Second, water can be added to enhance the recovery of TFA. Therefore, the effect of water on TDA recovery was studied. For these studies, 2.0 moles of TFA were reacted with one mole of MDTC. 2.1 Moles of toluene per mole of MDTC were used. Results of these studies are shown below in Table 3.

TABLE 3

Effect of Water on the TDA Yield

| gms water added (0.5M batch) | TDA net yield % based on MDTC |
|---|---|
| 0 | 92.0 |
| 10 | 91.8 |
| 20 | 91.9 |
| 30 | 91.6 |
| 35 | 89.2 |
| 40 | 88.7 |
| 50 | 83.7 |

The data in Table 3 show that the presence of up to 60 grams of water per mole of MDTC in the reaction medium did not adversely affect TDA net yields. When 1.5 moles of TFA were reacted with one mole of MDTC, however, a perceptible drop in TDA net yields was noticed at water levels of 30–40 grams of water per mole of MDTC (See Table 4, below).

TABLE 4

Effect of Water on TDA Yield

| gms water added (0.5M batch) | TDA net yield %* based on MDTC |
|---|---|
| 0 | 91.1 |
| 10 | 90.6 |
| 15 | 90.1 |
| 20 | 89.3 |
| 30 | 87.5 |
| 35 | 84.2 |
| 40 | 83.1 |

EXAMPLE 2

Recovery of TFA Using Base

Where molar excesses of TFA are used in the reaction with MDTC, it is desirable to recover the excess TFA. When pure TFA is mixed with about 99% pure toluene, it is possible to recover essentially all of the TFA via simple distillation techniques. This can be accomplished with or without water. However, only about 70% of the excess TFA is recoverable using simple distillation techniques from a reaction mixture, or from TDA in toluene, containing various by-products. Chemical routes of TFA recovery can also be used.

Studies were performed to determine the effects of alkali metal salts and acidification on recovery. Briefly, TFA in toluene was reacted with sodium hydroxide and various amounts of water. The mixture was then acidified with either HCl or $H_2SO_4$ and the recovery of TFA in the aqueous layer and toluene phase determined.

In a first study, excess TFA from the reaction with MDTC was converted to its sodium salt (TFA-Na) with 50% NaOH to remove it from the TDA reaction mixture as an aqueous solution. This procedure also permitted separation of the TFA from the bis-byproduct present in the TDA toluene phase. The TFA-Na salt/$H_2O$ mixture was treated with concentrated aqueous HCl to form a TFA/NaCl/$H_2O$ slurry. The TFA and $H_2O$ was then distilled in the presence of toluene returning to the column as reflux. After collecting all the aqueous TFA, toluene-TFA fractions were collected. At the end of the distillation, a small quantity of water was added to yield a concentrated slurry of NaCl and toluene. Approximately 81.5% of the TFA was removed from the pot as an aqueous solution. 15% of the TFA was found in the toluene fractions and 2.1% of the TFA remained in the reaction pot.

Acidification with $H_2SO_4$ resulted in much poorer TFA recoveries as compared to recoveries obtained with concentrated HCl or gaseous HCl containing known amounts of water. Data from simulation studies using NaCl or $Na_2SO_4$ are summarized in Tables 5 and 6, below. For the data in Table 5, 250 g toluene were charged with 0.5 moles of TFA (i.e., 50% excess from a 1 M run), 0.6 moles of NaCl and 45 g of water. For the data in Table 6, 250 g toluene were charged with 0.5 moles of TFA (i.e., 50% excess from a 1 M run), 0.30 moles of $Na_2SO_4$ and various amounts of water. In each case, the mixture was agitated and heated to reflux. The aqueous TFA and toluene-TFA overheads were collected. TDA runs were carried out a using 100% excess of TFA and the optimum amount of toluene. TFA recoveries were carried out using HCl gas.

TABLE 5

| Experiment Number | % Net TFA Recovery |
|---|---|
| 1 | 101.0 |
| 2 | 98.5 |
| 3 | 100.0 |

TABLE 6

| Exper. No. | grams $H_2O$ used | % net TFA Recovery |
|---|---|---|
| 1 | 30 | 84.5 |
| 2 | 45 | 86.2 |
| 3 | 60 | 86.8 |

The data in Tables 5 and 6 show that the recovery of TFA in the presence of $Na_2SO_4$ is poor. The data further show that the use of NaCl improved TFA recovery. The data in Table 6 show that TFA recovery can be enhanced by adding water to the salt prior to acidification. The amount of water used during the conversion of the sodium salt of TFA to the free acid with HCl gas had a major impact on the efficiency of the TFA recovery process. Table 7, below, shows the effects of added water on TFA recovery:

TABLE 7

| Amt of water/mole of recoverable TFA, added prior to HCl gas treatment | % TFA Recovery* |
|---|---|
| 0 g | 5 |
| 20 g | 50 |
| 40 g | 76 |
| 60 g | 99 |
| Conc. HCl sol'n in lieu of HCl gas | 99 |

EXAMPLE 3

Recovery of TFA Using Distillation

Toluene, recycled toluene/trifluoroacetic acid (TFA) (16 wt % TFA), fresh TFA, MDTC (less than 15% moisture) and recycled TFA (75 wt % TFA) are charged to a reaction vessel. After all the raw materials above are charged, the reactor is heated to 70° C.; this temperature is maintained for a cook-time of 1 hour.

The reaction mixture is heated to 115° C. while azeotroping toluene, water and TFA vapor from the reactor. The overhead vapors are condensed and the toluene phase is returned directly to the reactor. The water/TFA phase is drained to the TFA recovery surge tank.

At the end of the water removal, the reactor temperature is approximately 115° C. During distillation, the column serves as a pipe to. At this endpoint, the reaction mixture contains approximately 6 wt % of TFA, which is recovered.

The reactor temperature is increased from 115° C. to approximately 130° C. and the overhead condensate temperature increases from 73° C. to 115° C. during the distillation. At the end of the distillation the desired concentrations in the reactor are about 60 wt % TDA and the remainder toluene. The reactor is cooled to 70° C.

The reaction mixture still contains approximately 1 wt % of TFA. To purify the reaction mixture further approximately 20 wt % caustic is added to the reactor. This caustic forms the sodium salt of TFA and extracts the TFA from the organic phase to the aqueous phase. The phases are discharged from the reactor through a bag filter.

The product phases are separated and washed. The first separator removes the heavy aqueous phase from the organic phase. The organic stream is mixed with 70 wt % sulfuric acid in the mixer-settler. The $HSO_4$ protonizes the major impurity (bis-byproduct) and extracts it into the aqueous phase. The separation section of the mixer-settler removes the aqueous phase and combines it with the aqueous stream of the first separator for disposal. The TDA/toluene stream drains to the tank farm for storage for the following steps.

The TFA recovery is by a continuous distillation system. The TFA stream coming from the reactors is blended by circulation in the surge tank. The overhead product composition is essentially 100% water. The bottom product of the column contains 75 wt % of TFA with the remainder water. This stream is cooled and stored for recycle to the subsequent TDA batch.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process of making 2-(methylthio)-5-(trifluoromethyl)-1,3,4-thiadiazole comprising the steps of:
    (a) reacting methyldithiocarbazinate with a molar excess of trifluoroacetic acid in the absence of phosphoryl chloride, wherein the molar ratio of trifluoroacetic acid to methyldithiocarbazinate is from about 1.1:1 to about 5:1 and, wherein water is a by-product of reaction; and
    (b) recovering the excess trifluoroacetic acid.

2. The process of claim 1 wherein the molar ratio of trifluoroacetic acid to methyldithiocarbazinate is from about 1.25:1 to about 3.5:1.

3. The process of claim 2 wherein the molar ratio of trifluoroacetic acid to methyldithiocarbazinate is from about 1.25:1 to about 2:1.

4. The process of claim 1 wherein step (a) occurs at a temperature of from about 30° C. to about 150° C.

5. The process of claim 4 wherein step (a) occurs at a temperature of from about 60° C. to about 140° C.

6. The process of claim 1 wherein step (a) occurs in the presence of an aprotic, aromatic solvent.

7. The process of claim 6 wherein the solvent is toluene, xylene, cumene or mesitylene.

8. The process of claim 7 wherein the solvent is toluene.

9. The process of claim 8 wherein the toluene is present in an amount of at least about 0.5 moles of toluene per mole of methyldithiocarbazinate.

10. The process of claim 9 wherein the toluene is present in an amount of from about 1.5 moles of toluene per mole of methyldithiocarbazinate to about 3.0 moles of toluene per mole of methyldithiocarbazinate.

11. The process of claim 10 wherein the toluene is present in an amount of from about 2.5 moles of toluene per mole of methyldithiocarbazinate to about 3.0 moles of toluene per mole of methyldithiocarbazinate.

12. The method of claim 6 wherein the excess trifluoroacetic acid is recovered by distilling the solvent, water and trifluoroacetic acid.

13. The method of claim 12 wherein the solvent is toluene.

14. The process of claim 1 further comprising the step of recycling recovered trifluoroacetic acid to step 1 (a).

15. The method of claim 1 wherein the excess trifluoroacetic acid is recovered by distilling the water by-product and the trifluoroacetic acid.

16. A process of making 2-(methylthio)-5-(trifluoromethyl)-1,3,4-thiadiazole comprising the steps of:
   (a) reacting methyldithiocarbazinate with a molar excess of trifluoroacetic acid wherein water is a by-product of reaction;
   (b) heating reaction mixture to form vapors;
   (c) condensing the vapors to form a solvent phase and a trifluoroacetic acid/water phase; and
   (d) recovering the trifluoroacetic acid from the trifluoroacetic acid/water phase.

17. The process of claim 16 wherein step (a) occurs in the presence of an aprotic, aromatic solvent.

18. The process of claim 17 wherein the aprotic, aromatic solvent is toluene.

19. The process of claim 16 further comprising the step of recycling the recovered trifluoroacetic acid to step 1 (a).

20. A process of making 2-(methylthio)-5-(trifluoromethyl)-1,3,4-thiadiazole comprising the steps of:
   (a) reacting methyldithiocarbazinate with a molar excess of trifluoroacetic acid wherein water is a by-product of reaction;
   (b) heating reaction mixture to form vapors;
   (c) converting the excess trifluoroacetic acid to a trifluoroacetic-alkali metal salt; and
   (d) releasing free trifluoroacetic acid from the trifluoroacetic-alkali metal salt by acidifying the salt.

21. The process of claim 20 wherein step (a) occurs in the presence of an aprotic, aromatic solvent.

22. The process of claim 21 wherein the aprotic, aromatic solvent is toluene.

23. The process of claim 20 wherein the excess trifluoroacetic acid is reacted with an alkali metal hydroxide.

24. The process of claim 23 wherein the alkali metal hydroxide is sodium, potassium or lithium.

25. The process of claim 23 wherein the alkali metal hydroxide is sodium hydroxide.

26. The process of claim 23 wherein an amount of the alkali metal hydroxide relative to an amount of the excess trifluoroacetic acid is from about 1 to about 2 moles of the alkali metal hydroxide per mole of the excess trifluoroacetic acid.

27. The process of claim 20 wherein the trifluoroacetic-alkali metal salt is acidified with an inorganic acid.

28. The process of claim 27 wherein the inorganic acid is hydrochloric acid, sulfuric acid or nitric acid.

29. The process of claim 20 wherein water is mixed with the trifluoroacetic-alkali metal salt prior to acidification.

30. The process of claim 20 further comprising the step of recycling the recovered trifluoroacetic acid to step 1 (a).

* * * * *